US005708156A

United States Patent [19]
Ilekis

[11] Patent Number: 5,708,156
[45] Date of Patent: Jan. 13, 1998

[54] EPIDERMAL GROWTH FACTOR RECEPTOR-LIKE GENE PRODUCT AND ITS USES

[76] Inventor: John V. Ilekis, 4206 Linden, Western Springs, Ill. 60558

[21] Appl. No.: 658,883

[22] Filed: May 31, 1996

[51] Int. Cl.[6] .................. C07K 14/71; C07K 16/28; C12N 15/11; G01N 33/53
[52] U.S. Cl. .................. 536/23.5; 530/350; 530/399; 530/388.22; 530/387.7; 530/388.8; 530/389.7; 530/412; 514/12; 435/6; 435/7.1; 536/24.3
[58] Field of Search .................. 435/6, 7.1, 7.21, 435/7.23; 530/399, 350, 388.22, 387.7, 389.7, 388.8, 412; 536/23.5, 23.51, 24.3; 514/12

[56] References Cited

U.S. PATENT DOCUMENTS

| | | |
|---|---|---|
| 4,683,195 | 7/1987 | Mullis. |
| 5,218,090 | 6/1993 | Connors .................. 530/350 |
| 5,260,223 | 11/1993 | Brenner et al. .................. 436/501 |
| 5,424,191 | 6/1995 | Prasad et al. .................. 435/7.1 |

FOREIGN PATENT DOCUMENTS

| | | |
|---|---|---|
| 2712301 | 5/1995 | France. |
| 93/213171 | 10/1993 | WIPO. |
| 94/11531 | 5/1994 | WIPO. |
| 95/17205 | 6/1995 | WIPO. |

OTHER PUBLICATIONS

Carpenter, et al., Receptors for Epidermal Growth Factor and Other Polypeptide Mitogens. Ann. Rev. Biochem., 56:881–914 (1987).
Gusterson, et al., Cellular Localization of Human Epidermal Growth Factor Receptor. Cell. Biol. International Reports, 8:649–658 (1984).
O'Keefe, et al., Epidermal Growth Factor: Characteristics of Specific Binding in Membranes from Liver, Placenta, and Other Target Tissues. Arch. Biochem. Biophys., 164:518–526 (1974).
Sainsbury et al., Epidermal–Growth–Factor Receptor Status as Predictor of Early Recurrence of and Death from Breast Cancer. Lancet 1:1398–1402 (1987).
Scambia et al., Significance of Epidermal Growth Factor Receptor in Advanced Ovarian Cancer. J. Clin. Oncol., 10:529–535 (1992).
Mellon et al., Long–term Outcome Related to Epidermal Growth Factor Receptor Status in Bladder Cancer. J. Urol., 153:919–925 (1995).
Di Fiore et al., Overexpression of the Human EGF Receptor Confers an EGF–Dependent Transformed Phenotype to NIH 3T3 Cells. Cell, 51:1063–1070 (1987).
Riedel, et al., Ligand Activation of Overexpressed Epidermal Growth Factor Receptors Transfomrs NIH 3T3 Mouse Fibroblasts. Proc. Natl. Acad. Sci. U.S.A., 85:1477–1481 (1988).
Di Marco, et al., Autocrine Interaction Between TGFα and the EGF–receptor: Quantitative Requirements for Induction of the Malignant Phenotype. Oncogene, 4:831–838 (1989).

Todaro et al., Transforming Growth Factors (TGFs): Properties and Possible Mechanisms of Action. J. Supramolecular Structure and Cellular Biochemistry, 15:287–301 (1981).
Derynck et al., Synthesis of Messenger RNAs for Transforming Growth Factors α and β and the Epidermal Growth Factor Receptor by Human Tumors. Cancer Res., 47:707–712 (1987).
Kern et al., Growth Factor Receptors and the Progression of Breast Cancer. Semin. Cancer Biol., 1:317–328 (1990).
Weber et al., Production of an Epidermal Growth Factor Receptor–related Protein. Science, 224:294–297 (1984).
Merlino et al. Structure and Localization of Genes Encoding Aberrant and Normal Epidermal Growth Factor Receptor RNAs from A431 Human Carcinoma Cells. Mol. Cell. Biol., 5:1722–1734 (1985).
Sugawa et al., Identical Splicing of Aberrant Epidermal Growth Factor Receptor Transcripts from Amplified Rearranged Genes in Human Glioblastomas. Proc. Natl. Acad. Sci. U.S.A., 87:8602–8606 (1990).
Basu et al., Inhibition of Tyrosine Kinase Activity of the Epidermal Growth Factor (EGF) Receptor by a Trancated Receptor Form that Binds to EGF: Role for Interreceptor Interaction in Kinase Regulation. Mol. Cell Biol., 9:671–677 (1989).
Ishi et al., Characterization and Sequence of the Promoter Region of the Human Epidermal Growth Factor Receptor Gene. Proc. Natl. Acad. Sci. U.S.A., 82:4920–4924 (1985).
Haley et al., The Human EGF Receptor Gene: Structure of the 110 kb Locus and Identification of Sequences Regulating its Transcription. Oncogene Res., 1:375–396 (1987).
Johnson et al., Epidermal Growth Factor Receptor Gene Promoter. J. Biol. Chem. 263:5693–5699 (1988).
Ausubel et al., Current Protocols in Molecular Biology, vol. 2:10.8.1–10.8.13 (1992).
Ausubel et al., Current Protocols in Molecular Biology, vol. 2:11.0.1–11.2.22 (1992).
Ausubel et al., Current Protocols in Molecular Biology, vol. 2:15.0.1–15.6.10 (1992).
Ausubel et al., Current Protocols in Molecular Biology, vol. 1:4.6.1–4.10.7 (1992).
Ausubel et al., Current Protocols in Molecular Biology, vol. 1:9.0.3–9.14.3 (1992).
Ausubel et al., Current Protocols in Molecular Biology, vol. 1:16.0.05–16.19.9 (1992).

(List continued on next page.)

*Primary Examiner*—Stephen Walsh
*Assistant Examiner*—Claire M. Kaufman

[57] ABSTRACT

A novel human epidermal growth factor receptor-like protein has been identified, designated TEGFR. Provided herein is the nucleic acid sequence and deduced amino acid sequence of this protein. The invention relates to the measurement of its protein by immunological means or the measurement of its mRNA by recombinant DNA means in human biological samples. The invention also pertains to the use of its cDNA to produce a recombinant source of the protein. Moreover, the invention relates to its therapeutic use to inhibit the activity of epidermal growth factor receptor. Lastly, the invention also concerns the diagnostic and therapeutic use of this protein for human cancers.

16 Claims, 6 Drawing Sheets

OTHER PUBLICATIONS

Ausubel et al., Current Protocols in Molecular Biology, vol. 2:11.4.2–11.15.3 (1992).

Chomczynski et al. Single–Step Method of RNA Isolation by Acid Guanidinium Thiocyanate–Phenol–Chloroform Extraction. Anal. Biochem. 162:156–157 (1987).

Kashimata et al. Sex Difference in Epidermal Growth Factor Receptor Levels in Rat Liver Plasma Membrane. Endocrinol. 122:1707–1714 (1988).

Gill et al. Epidermal Growth Factor and Its Receptor. Mol. Cell. Endo., 51:169–186 (1987).

Ilekis et al., Expression of epidermal growth factor receptors at the mRNA and cell membrane levels in first trimester and term human placentae, Trophoblast Res., 5: 103–117, 1991.

Ilekis et al., Possible role of variant RNA transcripts in the regulation of epidermal growth factor receptor expression in human placenta, Mol. Reprod. Dev., 41: 149–156, Jun. 1995.

Ullrich et al., Human epidermal growth factor receptor cDNA sequence and aberrant expression of the amplified gene in A431 epidermoid carcinoma cells, Nature, 309: 418–425, May, 1984.

Flickinger et al., An alternatively processed mRNA from avian c–erbB gene encodes a soluble, truncated form of the receptor that can block ligand–dependent transformation, Mol. Cell. Biol., 12(2): 883–893, Feb. 1992.

Sambrook et al., Molecular Cloning, 2nd ed., Cold Spring Harbor, MA, pp. 14.14–14.15, 1989.

Wu et al., Huamn epidermal growth factor (EG) receptor sequence recognized by EGF competitive monoclonal antibodies, J. Biol. Chem., 264(29): 17469–17475, Oct. 1989.

Hillier et al., GenBank Database, Accession No. N29936, Jan. 5, 1996.

Petch et al., A truncated secreted form of the epidermal growth factor receptor is encoded by an alternatively spliced transcript in normal rat tissue, Mol. Cell. Biol., 10(6): 2973–2982, Jun. 1990.

Wu et al., Human epidermal growth factor receptor residue convalently cross–linked to epidermal growth factor, Proc. Natl. Acad. Sci. USA, 87: 3151–3155, Apr. 1990.

Salomon et al., Epidermal growth factor–related peptides and their receptors in human malignancies, Crit. Rev. Oncol. Hematol., 19(3): 183–232, Apr. 1995.

TEGFR >

EPIDERMAL GROWTH FACTOR RECEPTOR-LIKE GENE PRODUCT AND ITS USES

FIELD OF THE INVENTION

This invention relates to a novel human epidermal growth factor receptor-like protein. This invention encompasses its measurement in human biological samples and its diagnostic and therapeutic uses.

BACKGROUND OF THE INVENTION

Epidermal growth factor receptor, designated EGFR, is an important receptor involved in cellular growth and differentiation (Carpenter, et al., Ann. Rev. Biochem., 56:881–914 [1987]). It is expressed in a wide variety of cell types and tissues, (Gusterson, et al., Cell. Biol. International Reports, 8:649–658 [1974]; O'Keefe, et al., Arch. Biochem. Biophys., 164:518–526 [1984]). Particular attention has focused on the role of EGFR in the area of cancer research. Mounting evidence strongly suggests that aberrations in EGFR expression are involved in the etiologies of a number of cancers. A high incidence of elevated levels of EGFR are associated with diverse types of tumors including cancers of the breast, ovary, and bladder (Sainsbury et al., Lancet 1:1398–1402[1982], Scambi et al., J. Clin. Oncol., 10:529–535 9 [1992]; Mellon et al., J. Urol., 153:919–925 [1995]). In these cases, this overexpression is generally correlated with a poor prognosis for patient survival. Transfection studies in cell culture have shown that the overexpression of EGFR alone can induce a transformed phenotype and in the presence of one of its ligands, epidermal growth factor (EGF) or transforming growth factor-alpha (TGF-α), results in uncontrolled cell proliferation (Di Fore et al., Cell, 51:1063–1070 [1987]; Riedel, et al., Proc. Natl. Acad. Sci. U.S.A., 85. 1477–1481 [1988]; Di Marco et al., Oncogene, 4:831–838 [1989]). Some cancers overexpress both EGFR and TGF-α, and it is postulated that the aberrant co-expression of both the receptor and its ligand is an autotrine mechanism responsible for autonomous minor growth (Todoro et al., J. Supramolecular Structure and Cellular Biochemistry, 15:287–301 [1981]; Dernyck et al., Cancer Res., 47:707–712 [1987]). Since the overexpression of EGFR is associated with the invasiveness of certain cancers, this suggests that increased levels of the receptor may play a role in tumor progression. It is speculated that the acquistion of increased EGFR levels during tumor progression provides a tumor cell with a selective growth advantage for metastasis (Kern et al., Semin. Cancer Biol., 1:317–328 [1990]). Thus, the identification of substances that can be measured that would detect EGFR expressing cancers or agents that can be used to inhibit the activity of EGFR would be useful.

I have discovered a novel human EGFR-like protein. This substance which I have named TEGFR is highly related to EGFR (relevant preceding publications by the inventor concerning this invention are: Ilekis et al., In: Molecular Biology and Cell Regulation of the Placenta, pp 103–117 [1991]; Ilekis et al., Mol. Reprod. Dev., 41:149–156 [1995]). Similar types of EGFR related proteins have been described. These EGFR related proteins, however, are abnormal products of cancer cells or are recombinant products of the genetically engineered EGFR gene. Weber et al., Science, 224:294–297 (1984) described a soluble EGFR related protein of an approximately 100 kilodaltons (kD) molecular weight secreted by the human cancer cell line A431. Merlino et al., Mol. Cell. Biol., 5:1722–1734 (1985) cloned and characterized its 2.9 kilobase (kb) mRNA. He demonstrated that this RNA was generated as a result of an abnormal rearrangement of the EGFR gene. He also demonstrated that this transcript encoded a substantial portion of the 5' region of the EGFR gene, which contained the ligand binding domain of the receptor. Sugawa et al., Proc. Natl. Acad. Sci. U.S.A., 87:8602–8606 (1990) described similar types of EGFK gene rearrangment transcripts in gliomas. Basu et al., Mol. Cell. Biol., 9:671–677 (1989) showed that the 100 kD protein secreted by the A431 cell line can inhibit the activity of EGFR protein. Connors described a process described in U.S. Pat No. 5,218,090 in which the EGFK cDNA is genetically engineered to produce a number of recombinant proteins containing various portions of the ligand binding domain of EGFR. The molecular weights of these expressed proteins were 55, 68, and 85 kD.

My invention is also an EGFR related protein that contains a substantial portion of the ligand binding domain of the EGFK. My invention is novel, however, in that it is a normal protein produced by both normal and cancer cells. It is expressed in human placenta and in various human cancers. In contrast to the above mentioned EGFR related proteins, it is encoded by a mRNA of approximately 1.8 kb in length, and the molecular weight of its mature protein is approximately 80 kD. In addition, the cDNA sequence of TEGFR and its deduced amino acid sequence differs from these previously described EGFR related proteins and that of EGFK. Although, the etiolgy of this protein is unknown, it is favored by the inventor that it probably represents either an alternate splice product of the EGFR gene or a product of a different gene that is highly related to EGFR. The cDNA sequence of TEGFR is shown in "Sequence Listing" SEQ ID NO:1:. Support for these notions stems from its cDNA sequence, in which a significant portion of its cDNA shows identity to the 5'-region of the EGFR cDNA sequence. This is the region that contains the ligand binding domain of the receptor. The TEGFR cDNA sequence, however, diverges from that of the EGFR cDNA sequence in two regions. Divergence between the cDNA sequences of TEGFR and EGFR (Ullrich et al., Nature, 309:418–425 [1984]) occurs at the start of the 5'-untranslated region of TEGFR up to base 105 after which its sequence becomes homologous to the genomic EGFR promoter region. If TEGFR represents an alternate splice product of the EGFR and because of this sequence divergence at its 5' untranslated region, it is worth noting that the transcription site of TEGFR initiates further upstream from any of the previously shown transcription sites for the EGFR gene (Ishi, et al., Proc. Natl. Acad. Sci. U.S.A., 82:4920–4923 [1985]; Haley, Oncogene Res., 1:375–396 [1987] Johnson, et al J. Biol. Chem., 263:5693–5699 [1988]). The TEGFR sequence also diverges from that of EGFR starting at the last two codons of the open reading frame of TEGFR and continues into its 3'-untranslated region. This later divergence results in a deduced protein of 381 amino acids that contains the sequence Met-24 to Gly379 of the EGFR protein with the additional novel amino acid sequence Leu380-Ser381 at its carboxy terminus.

Although TEGFR is highly related to EGFR, its cDNA sequence and its deduced amino acid sequence is novel. In summary, some of the characteristics of TEGFR that distingushes it from the previously mentioned EGFR related proteins and EGFR include: (1) A deduced amino acid length of 381; (2) A mature and soluble protein of approximately 80 kD; (3) The last two carboxy terminal amino acids consisting of the sequence Leu380-Ser381; (4) Unique nucleotide sequence regions at base regions 1–105 and 1713–1828, inclusive.

These characteristics of TEGFR allows the ability to measure the TEGFR protein or its mRNA distinctly from that of EGFR in human biological samples. Its unique carboxy terminus amino acid sequence allows the ability to generate TEGFR specific antibodies. Moreover, the discoveries that the TEGFR protein can inhibit the activity of EGFR and that the measurement of its protein or its mRNA can detect EGFK expressing cancers encompasses some of its useful purposes. Hence the invention incorporates useful methods for the measurement of TEGFR. In addition, my invention also incorporates the therapeutic and diagnostic use of TEGFR. Further objects and advantages of my invention will become apparent from a consideration of the figures, ensuing description, and examples.

SUMMARY OF THE INVENTION

This invention relates to the discovery of a novel human EGFR-like protein having an approximate molecular weight in the range of 80,000 daltons and the cDNA sequence encoding this protein. TEGFR is a normal and natural protein that is similar to the ligand binding domain of EGFR, said protein and its mRNA being detectable in human biological samples. Several embodiments of this invention relates to the measurement of TEGFR in human biological samples either by immunological or recombinant DNA means. Another embodiment of this invention concerns the use of its cDNA sequence to produce a recombinant form of the said protein. In another embodiment, this invention relates the use of this protein as an agent to inhibit the activity of human EGFR. A final embodiment of the invention concerns the use of the measurement of TEGFR to detect EGFR expressing cancers.

BRIEF DESCRIPTION OF THE FIGURES

FIG. 1A shows detection of TEGFR in human placenta. FIG. 1B shows detection of TEGFR, in human breast and ovarian cancers.

FIG. 2A shows reverse transcriptase-PCR detection of TEGFR. FIG. 2B shows Northern blot detection of TEGFR.

FIG. 4A shows the level of TEGFR in human breast cancers. FIG. 4B shows the correlation between the level of EGFR and TEGFR in human breast cancers.

FIG. 5A shows the level of TEGFR in human ovarian cancers. FIG. 5B shows the correlation between the level of EGFR and TEGFR in human ovarian cancers.

DETAILED DESCRIPTION OF THE INVENTION

Figure 1A:
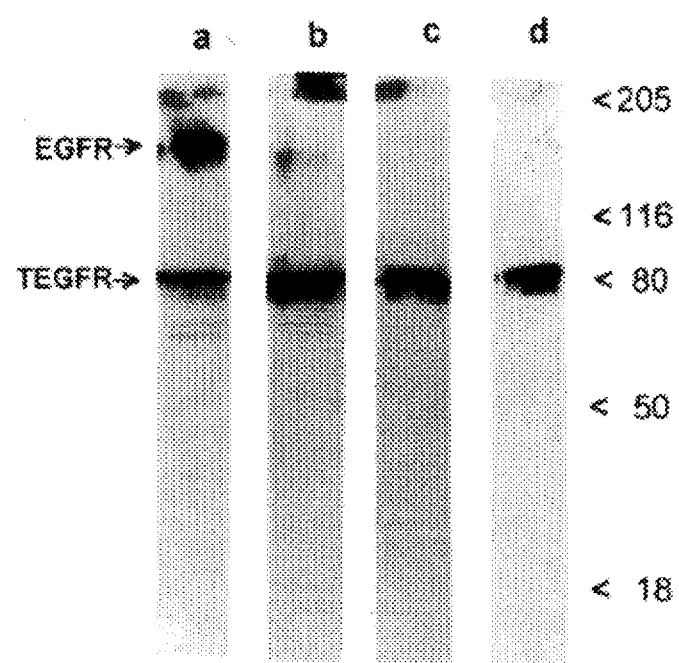
FIGS. 1A and 1B shows immunological detection of TEGFR by Western blot.

This invention is concerned with an EGFR-like protein, termed TEGFR. The mature protein having an molecular weight of approximately 80,000 daltons. The invention is also concerned with uses derived from its cDNA sequence and deduced amino acid sequence. The objects of the invention are: (a) means to detect or measure TEGFR protein and mRNA, (b) use of the TEGFR protein to inhibit the activity of EGFR, (c) production of the TEGFR protein by DNA recombinant means, (d) means for detecting EGFR expressing cancers.

One embodiment of the invention concerns a method for the measurement of the TEGFR protein by immunological means. This method uses an antibody, designated A, that specifically binds to TEGFR and comprises the steps of:

(a) Adding antibody A to a sample containing TEGFR;

(b) Allowing antibody A to bind to TEGFR;

(c) Removing unreacted antibody A;

(d) Detecting the antibody A-TEGFR complex.

The sample being a human biological sample and can include and is not limited to fixed tissue for pathological examination, biological fluids such as serum or urine, or extracted tissue or biological fluids components attached to a solid support such as in Western blot analysis. Of course, antibody A can include an antibody that binds to any portion of TEGFR protein. Moreover, there are a number of different means for the immunological detection of proteins to those versed in the art and is generally described in Ausubel et al., Current Protocols in Molecular Biology Vol. 2:10.8.1–10.8.13 & 11.0.1–11.2.22 (1992), and is hereby incorporated by reference. The preferable method being an antibody binding the carboxy terminus of TEGFR. The detection of the antibody A-TEGFR complex can be accomplished by a number of different ways to those versed in the art. This can include and not limited to antibody A being labelled with an enzyme or other type of detection molecule. Alternatively, another antibody or other type of protein can be used that binds to antibody A and is labelled either with an enzyme or other detection molecule. Detection of the label can be qualitative or quantitative, and the detection method can include and is not limited to colorimetric, chemiluminence, spectrophotometric, radiometric, densitometric or fluorometric means.

Another embodiment of the invention relates to the measurement of TEGFR mRNA in human biological tissues and fluids using the recombinant DNA method known as "polymerase chain reaction" or PCR, as described in U.S. Pat. No. 4,683,195. This method generally relies on the enzymatic amplification of a segment of DNA using specific oligonucleotide primers that flank a desired DNA sequence to be amplified. Oligonucleotide primers are generally a short nucleotide sequence of DNA or RNA. Besides the detection of DNA, mRNA for a particular gene can be detected by a method called "reverse transcriptase-PCR" using PCR by generating DNA from the mRNA using the enzyme reverse transcriptase. These are methods known to those versed in the art and is generally described in Ausubel et al., Current Protocols in Molecular, Vol 2:15.0.1–15.6.10 (1992), and is hereby incorporated by reference. One of the embodiments of this invention is to use primer sequences that are based on the cDNA sequence of TEGFR for the measurement of TEGFR mRNA by reverse transcriptase-PCR and comprises the steps of:

(a) Synthesizing cDNA from RNA obtained from tissue or biological fluids using reverse transcriptase;

(b) Amplifying a segment of TEGFR cDNA by using primers that flank the said segment;

(c) Detecting the TEGFR DNA amplified product.

Primers used to amplify a segment of TEGFR cDNA includes two primers that flank a region of the TEGFR cDNA sequence. One of these primers having a sense sequence and the other having an antisense sequence contained within the cDNA sequence of TEGFR. Of course, the sequence of said primers can be identical or nearly identical to a sense or an antisence sequence contained within the cDNA of TEGFR. One of the preferred methods of this invention utilizes at least one primer whose sequence is identical or complementary to a portion of the cDNA TEGFR sequence, said sequence being contiguous with and containing a sequence that is encompassed within the base regions spanning bases 1–105 or 1713–1828 of the TEGFR cDNA sequence. These base regions are unique sequence regions not contained within the EGFR cDNA sequence. Detection of the TEGFR DNA amplified product can be either qualitative or quantitative and the detection method can include but is not limited to colorimetric, chemiluminence, spectrophotometric, radiometric, densitometric or fluorometric means.

Another embodiment of the invention relates to the measurement of TEGFR mRNA by hybridization methods. These methods rely on the use of a sequence of DNA or RNA that is labelled and complementary to a sequence contained within a mRNA of interest. The labelled probe hybridizes or binds to said mRNA that is to be measured. Hybridization methods can include but is not limited to Northern blot analysis and RNase protection assays. These methods are known to those versed in the art and examples of these methods can be generally found in Ausubel et al., Current Protocols in Molecular Biology, Vol 1:4.6.1–4.10.7 (1992), and is hereby incorporated by reference. One of the embodiments of the invention is the use of hybridization probes that are complementary to portions of the TEGFR cDNA sequence for the measurement of TEGFR and comprises the steps of:

(a) Adding said probe to a sample containing TEGFR mRNA;

(b) Allowing the probe to hybridize to TEGFR mRNA;

(c) Removing unhybridized probe;

(d) Detecting hybridized probe.

One of the preferred methods of this invention utilizes a probe, either DNA or RNA, whose sequence is identical or complementary to a portion of the cDNA TEGFR sequence, said sequence being contiguous with and containing a sequence that is encompassed within the base regions spanning bases 1–105 or 1713–1828 of the TEGFR cDNA sequence. These base regions are unique sequence regions not contained within the EGFR cDNA sequence. This probe can be chemically or enzymatically synthesized. Said probe being labelled with a detection molecule. The detection molecule can include but is not limited to a radioactive isotope or small molecular weight molecule that can bind to an antibody or other type of binding protein and subsequently detected enzymatically. Detection of the label can be either qualitative or quantitative and the detection method can include and is not limited to colorimetric, chemiluminence, spectrophotometric, radiometric, densitometric or fluorometric means.

Another embodiment of my invention is the use of the TEGFR protein to inhibit the activity of EGFR. TEGFR obtained either from a human source or produced by DNA recombinant means can be used for this purpose. While the role of TEGFR is unknown in the human, the administration of TEGFR may be beneficial to certain individuals, particularly those individuals with cancer in which the cancer growth is dependent on the activity of EGFR. TEGFR may be therapeutically administrated by several different routes including but not limited to TEGFR contained in physiological acceptable carriers, excipents, or stabilizers in the form of lyophilized cake or aqueous solutions. TEGFR may be optionally combined with or administrated in concert with other agents known for use in the treatment of human diseases, such as malignancies. TEGFR may be administrated in accord with but not limited to known methods such as injection or infusion by intravenous, intraperitoneal, intramuscular, or intraarterial, or by sustained release systems to those famaliar with the art.

Another embodiment of the invention relates to the production of the TEGFR protein by DNA recombinant technological means. These methods are known to those versed in the art and is generally described in Ansubel et al., Current Protocols in Molecular Biology, Vol 1: 9.0.3–9.14.3 & Vol 2: 16.0.05–16.19.9 (1992), and is hereby incorporated by reference. This embodiment encompasses the use of the TEGFR cDNA coding sequence for insertion into a suitable protein expression vector and comprises the following steps:

(a) Inserting TEGFR cDNA into an appropriate protein expression vector to generate a recombinant DNA molecule;

(b) Transfecting the recombinant DNA molecule into a host cell.

Of course, the entire cDNA or a portion of the cDNA coding for the entire or a portion of the open reading frame of the TEGFR cDNA sequence can be inserted into a suitable expression vector for protein expression. One of the preferred methods includes the insertion of the entire open reading frame of TEGFR bounded by bases 504–1718. The vector can comprise any known or commercially available expression vectors including but not limited to plasmids, phagemids and the like. The introduction of the recombinant molecule can be introduced by various methods including but not limited to chemical means, extroporation, viral infection, lipid mediated fusion or similar methods of introduction. The host can be and is not limited to mammalian cells either in cell culture or in an intact mammal including human, bacterial culture, yeast culture, insect culture or the like.

Another embodiment of my invention is the production of antibodies against TEGFR. This can include using the entire TEGFR protein or portions of the TEGFR protein as antigens for the production of antibodies. The production of antibodies are methods known to those versed in the art and is generally described in Ausubel et al., Current Protocols in Molecular Biology, Vol 2: 11.4.2–11.15.3 (1992), and is incorporated by reference. One of the preferred methods includes the synthesis of short peptides based on the deduced and no acid sequence of the TEGFR cDNA sequence to use as an antigen to generate antibodies against TEGFR. This would include but is not limited to the synthesis of a short peptide that has an amino acid sequence contiguous with and containing the carboxy terminus of the TEGFR amino acid sequence, and said peptide would contain either Leu380 or Leu380-Ser381 at its terminal end. These antigens can be used alone or conjugated to other carriers to be immunogenic in the species to be immunized for the production of antibodies. These antibodies can either be produced in an animal and harvested from its blood (commonly known as polyclonal antibodies) or the animal's antibody-producing cells fused with another type of cell which is then cultured to produce the antibody and is harvested from the culture media (commonly known as monoclonal antibodies).

An additional embodiment of my invention relates to the measurement of TEGFR for detecting EGFR expressing human cancers. Cancers that express EGFR also generally express TEGFR. Consequently, the measurement of TEGFR would be useful for detecting EGFR expressing cancers in human biological samples. The biological sample used can be but is not limited to blood and its components plasma or serum, urine, or tissue extracts. The modes of measurement of TEGFR can be either qualitative or quantitative and can include but are not limited to immunological or DNA recombinant means, as described in the earlier embodiments.

The examples discussed below are intended to illustrate some of the uses of the invention and should not be construed as limitations.

EXAMPLE 1

Immunological Detection of TEGFR

A. Western Blot Analysis of Human Placenta

Term placental tissue was homogenized using a Polytron homogenizer (Brinkmann Instruments, Westbury, N.Y.) in homogenization buffer (50 mM HEPES, 1 mM PMSF, 100 KU/ml aprotinin, 1 μ/ml leupeptin, 5 mM EDTA; pH 7.6) at 4° C. The homogenate was centrifuged at 1500×g to remove unbroken cells, and the supernatant further fractionated into microsomal and soluble fractions by ultracentrifugation at 100,000×g for 30 min at 4° C. The microsomal fraction, following 3 washes and final resuspension in homogenization buffer, and soluble fraction were stored frozen at −70° C. until further processing.

Western blot analysis was performed using a monoclonal antibody (#05-104; Upstate Biotechnology Inc., Lake Placid, N.Y.) recognizing the Ala351–Asp364 sequence of the ligand binding domain of human EGFR (Wu et al., Proc. Natl. Acad. Sci. U.S.A., 87:3151–3155, [1990]). This antibody is designated LBD Ab for ligand binding domain antibody. LBD Ab also recognizes TEGFR, since TEGFR also contains the same recognition epitope. Proteins were fractionated using 1% SDS-polyacrylamide (7.5%) gel electrophoresis and electroblotted onto a nitrocellulose membrane (BioRad Laboratories, Richmond, Calif.). The blot was preincubated for 3 hrs at 4° C. in TST (50 mM Tris-HCl, 150 mM NaCl, 1% Tween 20; pH 7.4) containing 5% (w/v) nonfat dry milk (Blotto), followed by an overnight incubation at 4° C. with LBD Ab at a concentration of 1 μg/ml in 5% Blotto-TST. Following the incubation, the blot was rinsed (3×) and washed (2×15 mins) in 5% Blotto-TST. The blot was reincubated with goat anti-mouse IgG coupled to horseradish peroxidase (BioRad Laboratories) for 2 hrs at RT. Following the incubation with the secondary antibody, the blot was rinsed and washed in TST (3×15 mins). Immunodetection was performed using an enhanced chemiluminescence detection system as recommended by the manufacturer (ECL, Amersham Corp, Arlington Heights, Ill.).

FIG. 1A shows Western Blot results of human placenta. Human placental tissue was fractionated into a 100,000×g microsomal and soluble fraction. The soluble fraction was further subjected to affinity chromatography using the ligand binding domain antibody (LBD Ab) or EGF as the absorbent. 50 μg of protein from the microsomal (lane a) and soluble (lane b) fractions and 5 μg of protein from each of the affinity column purifications, LBD Ab (lane c) and EGF (lane d), were analyzed by Western blot analysis using LBD Ab. The results show that TEGFR can be immunologically detected in a human biological sample at approximately 80 kD (lane a) distinctly from that of EGFR at approximately 170 kD. The results also show that TEGFP, is a soluble protein (lane b). The results further show that TEGFR can be bound by either an affinity column containing LBD Ab (lane c) or EGF (lane d), a ligand for EGFR.

B. Western Blot Analysis of Breast and Ovarian Cancers

Frozen tissues were pulverized on dry ice and immediately homogenized in homogenization buffer as previously described for placental tissue. The tissue homogenates were centrifugation at 1500×g to remove unbroken cells and large particulates. An aliquot from the resulting supernatant fractions was used for protein determination and the remainder of the supernatant was stored at −70° C. until Western blot analysis. A portion of the supernatant was diluted in gel loading buffer to a final concentration of 1 mg/ml and 25 μl (25 μg protein) was used for Western blot analysis. Proteins were fractionated by SDS-PAGE. A polyacrylamide concentration of 8% was used. Following SDS-PAGE, the proteins were electroblotted onto a nitrocellulose membrane and Western blot analysis was performed as previously described with the exception that a concentration of 10 μg/ml of the monoclonal ligand binding domain antibody (LBD Ab) was used for immunodetection.

Figure 1B:
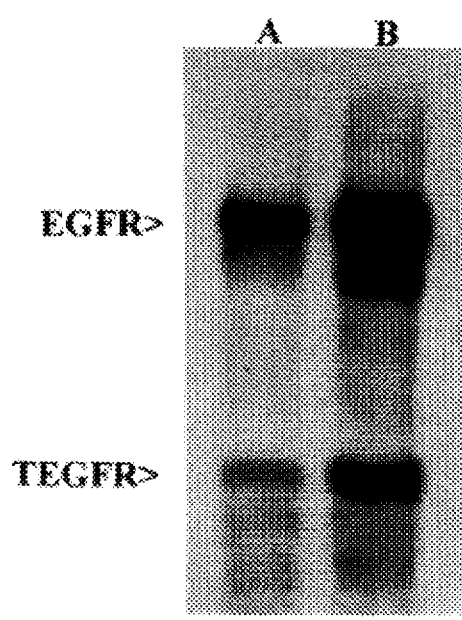

FIG 1B shows Western blot results of human cancers. Lane A is a human breast cancer specimen. Lane B is an ovarian cancer specimen. The results show that TEGFR can be immunologically detected in human cancers by Western blot analysis.

EXAMPLE 2

Recombinant DNA Detection of TEGFR

A. Reverse-transcriptase-PCT of TEGFR

Two primers were designed based on the cDNA sequence of TEGFR using the computer program Primer Premier Version 3.0 (Premier Biosoft International, Palo Alto, Calif.). Primers were synthesized by conventional methods. Primer 1 corresponded to a sense primer corresponding to the region of bases 1352–1373 inclusive within the open reading frame of TEGFR with the following sequence: 5'CAAATACAGCTTTGGTGCCACC. Primer 2 corresponded to an antisense primer corresponding to the region of bases 1773–1792 inclusive within the 3'-untranslated region of TEGFR with the following sequence: 5'AGGGAACAGGAAATATGTCG. PCR amplification of TEGFR cDNA using this primer pair results in a 440 bp product.

Total RNA was isolated using the method of Chomczynski and Sacchi, Anal. Biochem. 162:156–157 (1987) from the following: human term placental tissue, human breast cancer cell lines (MCF-7, T47D, MDA-MB-436), a human ovarian cancer cell line (OVCAR-3), and a human prostate cancer cell line (LnCap). One μg of total RNA was used to synthesize cDNA by the oligo-dT priming method in a final total volume of 25 μl using a commercial RT-PCR kit (Perkin Elmer, Foster City, Calif.) according to the instructions of the supplier. PCR reaction was performed as follows: One μl of the above reaction was used for amplification to detect TEGFR by PCR using a commercial kit (TaKaRa Ex Taq, Pan Vera Corp., Madison Wis.). The final volume of the PCR reaction mixture was 25 μl and the reaction mixture contained the following: 14.5 μl water, 2.5 ml of 10× buffer, 1.5 μl of dNTPs (33 mM of each dNTP), 1 μl of 15 mM of primer 1, 1 μl of 15 mM primer 2, 1 μl of cDNA, and 1 μl of Taq polymerase (0.5 U/μl). The PCK conditions were: 1 min denaturation at 94° C., 30 sec annealing at 60° C., and 30 sec extension at 72° C. Amplification was for 35 cycles using a PTC-100 thermal cycler with a Hot Bonnet (MJ Research, Watertown, Mass.). A 5 μl aliquot of each PCR reaction was analyzed by agarose (1.5%) gel electrophoresis and DNA visualized by ethidium bromide. Although the analysis is a visual assessment and therefore qualitative in nature, it is possible to quantify the results. This could be done by various means, one of which is by densitometry.

Figure 2A:
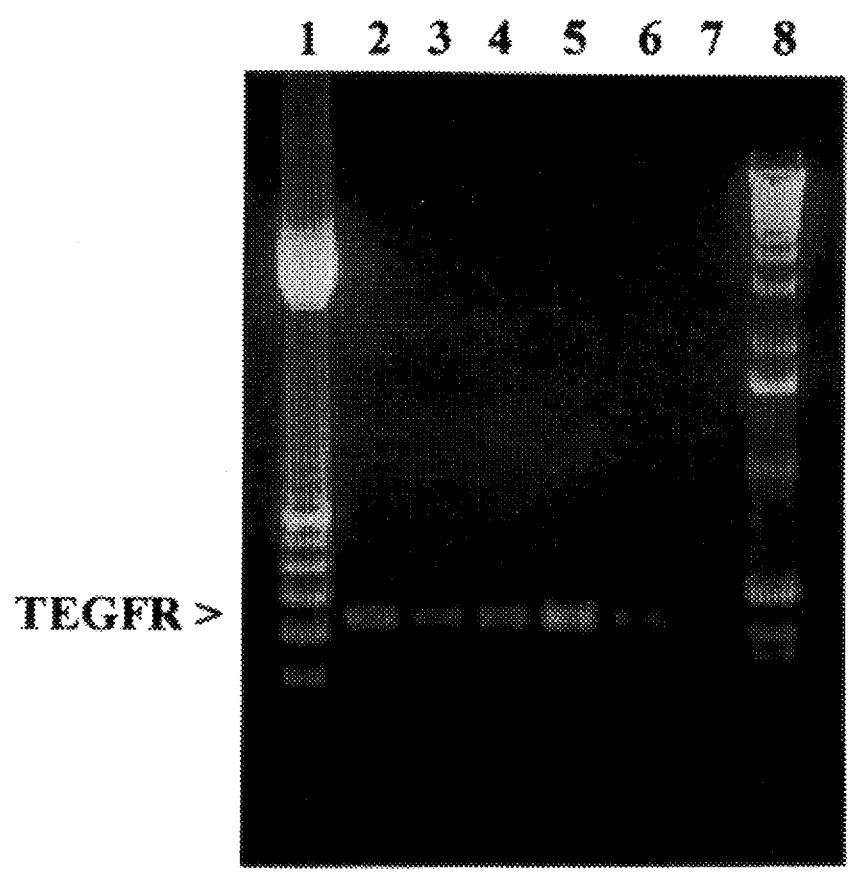
FIGS. 2A and 2B shows recombinant DNA detection of TEGFR.

FIG. 2A shows the reverse transcriptase-PCR results: lane 1 (DNA standard A), lane 2 (placenta), lane 3 (LnCap cells), lane 4 (OVCAR-3 cells), lane 5 (MDA-MD-436 cells), lane 6 (T47D), lane 7 (MCF-7 cells), and lane (DNA standard B). The results show that TEGFR can be detected by recombinant DNA means using reverse-transcriptase-PCR both in normal tissue (lane 2) and in human cancer cells (lanes 3–7) known to express EGFK. The results also show generally a correlation between the level of TEGFR detected and the expression level of EGFR. For example, MCF-7 cells which express a very low level of EGFR show a barely detectable band corresponding to TEGFR (lane 7). In contrast, MDA-MD-468 cells which express a very high level of EGFK show a very strong band corresponding to TEGFR (lane 5).

B. Northern Blot Detection of TEGFR

Total RNA was obtained by ultracentrifugation of tissue homogenized in a solution containing guanidine thiocyanate layered on a cushion of CsCl, and was followed by two ethanol precipitations of the isolated RNA dissolved in a solution containing guanidine hydrochloride (Ilekis et al., In: Molecular Biology and Cell Regulation of the Placenta, pp 103–117 [1991]) PolyA+RNA was obtained from total RNA by selective binding to oligo-dT cellulose. Northern blot analysis was performed using standard methodology. PolyA+RNA (1 μg) was size fractionated using 2.2M formaldehyde-1.0% agarose gel electrophoresis and the RNA transferred to nylon membranes (Gene Screen; New England Nuclear, Boston, Mass.) by electroblotting.

The plasmid p5'-E7 (Ilekis et al., Mol. Reprod. Dev., 41:149–154 [1995]) containing a cDNA insert corresponding to base pairs 610–1347 of the human EGFR cDNA was used to generate a probe that hybridizes to a common sequence contained in both EGFR and TEGFR mRNA. The plasmid pJZL containing a cDNA insert corresponding to base pairs 1620–1868 of the human TEGFR cDNA was used to generate a probe that hybridizes only to TEGFR mRNA. This probe sequence corresponded mainly to the 3'-untranslated region of TEGFR. The inserts in both these plasmids are flanked by viral promoters for the generation of antisense RNA probes. Antisense RNA probes were generated using a commercial kit (Promega. Madison, Wis.). Probes were synthesized from p5'-E7, linearized with Cla I, by in-vitro transcription driven by SP6 polymerase in the presence [32P]CTP (3000 Ci/mmole). A probe was synthesized from pJZL, linearized with BamH I, driven by T7 polymerase using [32P]UTP (3000 Ci/mmole) as the label. The specific activities of the probes were approximately $10^8$ dpm/ug.

Hybridization of duplicate Northern blots was performed overnight using either the EGFR or TEGFR RNA probe. Hybridization was performed at 57° C. The blots were prehybridized for 3 hrs then hybridized overnight. (The prehybridization and hybridization solution [plus probe] consisted of 50% formamide, 6XSSC, 10% dextran sulfate, 0.5% nonfat dry milk, 1% SDS, 250 ug/ml of both sheared salmon sperm DNA and yeast RNA.) Post hybridization washes (3×30 mins at 68° C.) were using 2XSSC-1% SDS, followed by 0.1XSSC-1% SDS and included a final RNase A digestion (10 μg ml in 2XSSC-0.1% SDS) step for 1 hr at 37° C. Hybridization was detected on X-ray film by radioautography.

Figure 2B:
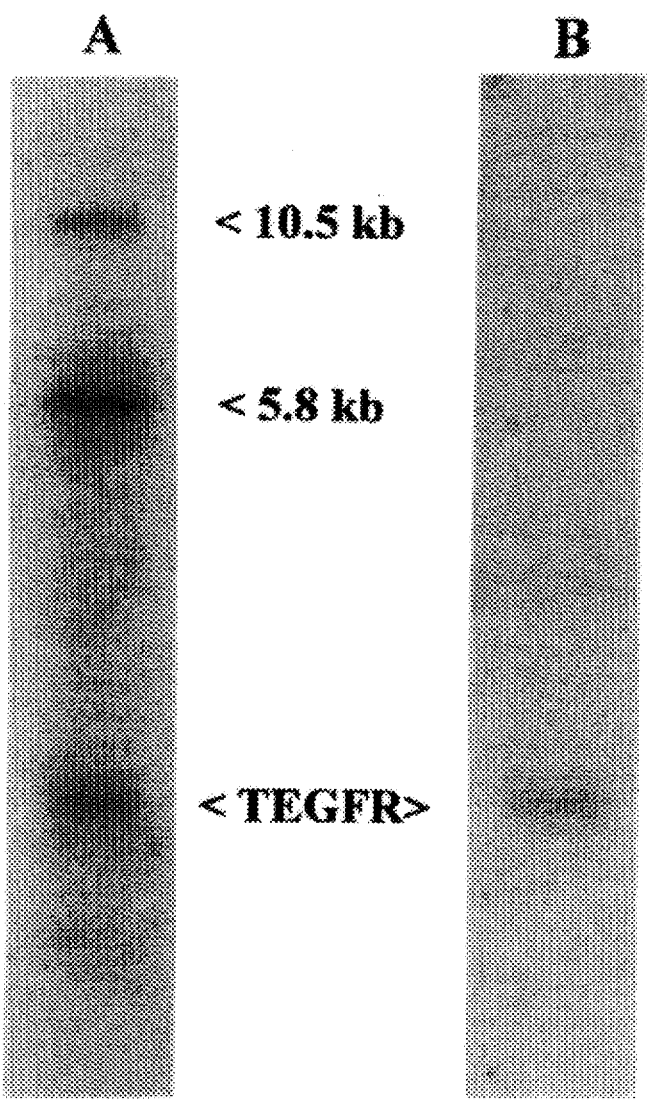

FIG. 2B shows the Northern blot results. Lane A shows a Northern blot hybridized with the EGFR probe that hybridizes to both EGFR (10.5 kb and 5.8 kb) and TEGFR (1.8 kb) mRNAs. Lane B shows a duplicate Northern blot hybridized with the TEGFR probe that hybridizes to only TEGFR mRNA. The results show that TEGFR mRNA can be detected specifically from that of EGFR mRNA using a TEGFR probe sequence.

EXAMPLE 3

Inhibition of EGFR Activity by TEGFR

A. Purification of TEGFR

An enriched TEGFR preparation was obtained by affinity chromatography. Affinity chromatography columns were made by coupling either the ligand binding domain antibody (LBD Ab) described previously for Western blot analysis or human EGF (Amgen, Thousand Oaks, Calif.) to CNBr activated Sepharose 6MB (Pharmacia LKB Biotechnology, Piscataway, N.J.). One hundred μg of LBD Ab or EGF was coupled per 0.3 gr of CNBr-Sepharose essentially as described by the manufacturer. Crude purification of TEGFR was performed by incubating the 100,000×soluble fraction of a human term placenta homogenate, as previously described, supplemented to 150 mM NaCl and 0.1% Triton X-100, with an equal bed volume of EGF conjugate overnight at 4° C. with gentle rocking in a sealable column. Following the incubation, the column was drained and washed with 5 column bed volumes of wash buffer (50 mM NaPO$_4$, 500 mM NaCl, 1% Triton X-100; pH 6.3). TEGFR was then eluted with 5 column bed volumes of elution buffer (50 mM glycine, 150 mM NaCL, 0.1% Triton X-100; pH 2.5) into a tube containing 0.2 volumes of 1M Tris-HCl, pH 9.0. The TEGFR fraction was concentrated by ultrafiltration using a Centricon-30 concentrator (Amicon Inc., Beverly, Mass.) to a volume of approximately 1/10th of the original starting soluble fraction volume. The concentrated crude TEGFR fraction following elution from the EGF affinity column was diluted 10× with homogenization buffer and processed using LBD Ab as the absorbent as previously described. The TEGFR preparation was concentrated by ultrafiltration, adjusted to a total protein concentration, and stored at -70° C. until use.

B. In Vitro EGFR Autophosphorylation Assay

Autophosphorylation of EGFR was performed based on the method described by Kashimata et al., Endocrinol. 122:1707–1714 (1988). Autophosphorylation is an intrinsic activity of EGFR (Gill et al., Mol. Cell. Endo., 51:169–186 [1987]). Placental membranes were isolated and EGFR levels in the membrane preparation was quantified by Scatchard plot analysis as previously described (Ilekis et al., In: Molecular Biology and Cell Regulation of the Placenta, pp 103–117 [1991]). One hundred μg of placental membrane protein containing approximately 300 fmoles of EGFR was incubated in the absence or presence of 100 nM of EGF containing various amounts of TEGFR (0–10 μg total protein) in a total volume of 40 μl for 40 mins. The reaction was initiated by the addition of 20 μl of a reaction mixture to give a final concentration of 50 mM [32P]ATP(1 mCi/ nm), 5 mM MnCl$_2$, 5 mM MgCl$_2$, 100 mM orthovanadate and 15 mM NaF. Following a 1 minute incubation, placental membranes were pelleted by high speed centrifugation (15 mins at 12,000×g), washed and radioactivity measured in a scintillation counter.

Figure 3:
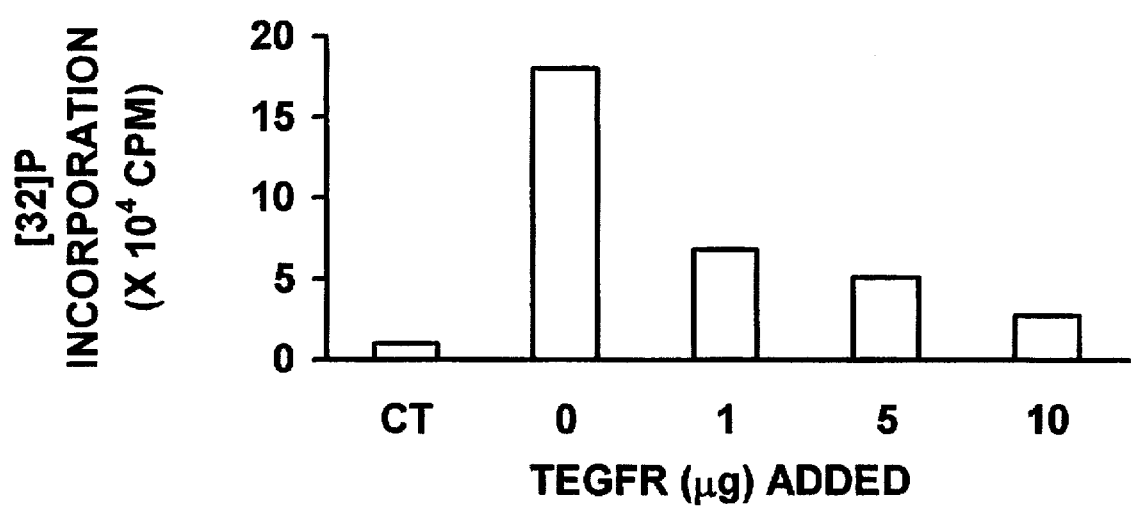
FIG. 3 shows results of TEGFR inhibiting EGFR activity.

FIG. 3 presents the autophosphorylation assay results. The results show that TEGFR inhibits the autophosphorylation of EGFR in a dose dependent manner with greater than 50% inhibition obtained at a dose 1 μg. Note a low incorporation of $^{32}$P in the absence of EGF (CT). This result demonstrates the ability of TEGFR to inhibit the activity of EGFR.

EXAMPLE 4

Detection of Human EGFR Expressing Cancers by TEGFR Expression

A total of 24 breast specimens were analyzed for EGFR and TEGFR expression by Western blot analysis. These included 7 normal breast tissues and 17 breast cancers. The breast cancers consisted primarily of ductal carcinomas, the most prevalent form of breast cancer. Expression levels for both TEGFR and EGFR were quantified by densitometry, following Western blot analysis, as previously described, and are expressed as relative densitometry units. It may be possible to convert densitometry units presented herein to absolute units such as fmol/mg of total protein. Statistical significance was determined by linear regression analysis. A $p<0.05$ was considered statistically significant.

Figure 4A:
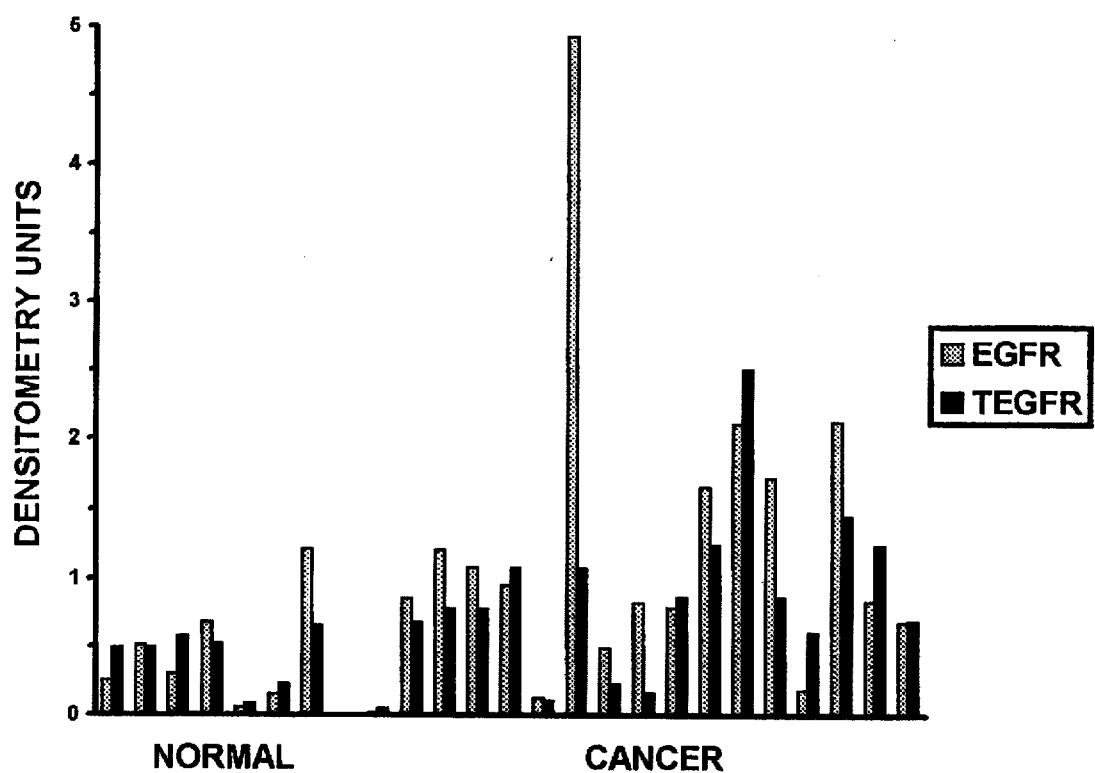
FIGS. 4A and 4B show the measurement of TEGFR in human breast cancers.
Figure 4B:
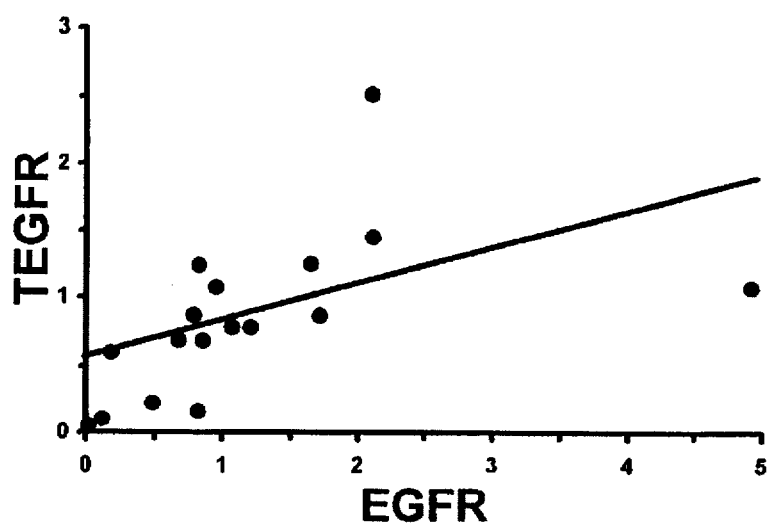

FIG. 4A displays the individual levels of EGFR and TEGFR obtained in these specimens. The results of this analysis indicated that EGFR and TEGFR were both expressed in all normal and breast cancer specimens. The number of breast cancers that express levels above the highest normal individual value for TEGFR was 10. This number represents 59% of breast cancers with elevated levels of TEGFR above normal. FIG. 4B shows the correlation between EGFR and TEGFR levels obtained from 17 breast cancers. A significant correlation ($r=0.52$, $p<0.032$) is obtained between the level of EGFR and TEGFR.

To determine if the measurement of TEGFR could be used to detect other types of cancers that express EGFR, a total of 26 ovarian cancers were also analyzed similarly by Western blot. The ovarian cancers consisted of cystadenocarcinomas the most prevalent form of ovarian cancer.

Figure 5A:
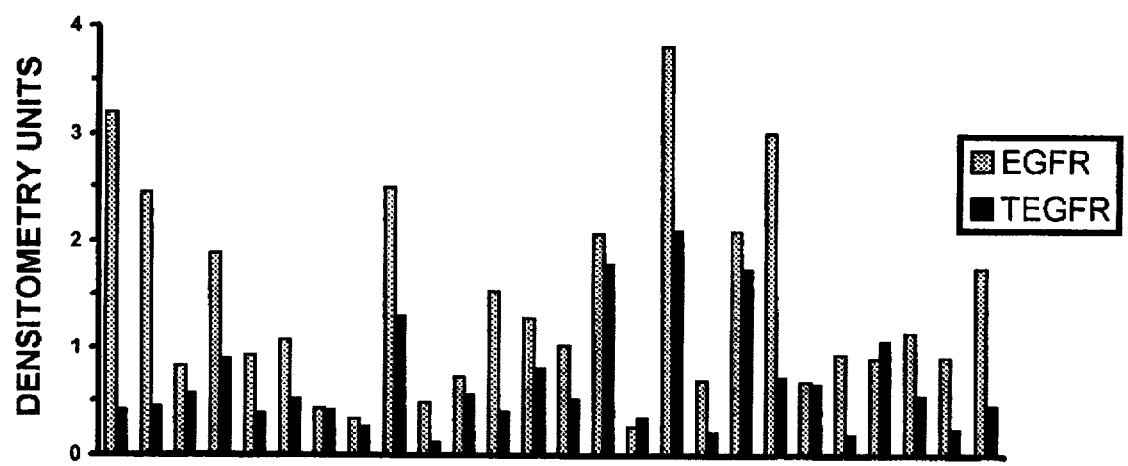
FIGS. 5A and 5B show the measurement of TEGFR in human ovarian cancers.
Figure 5B:
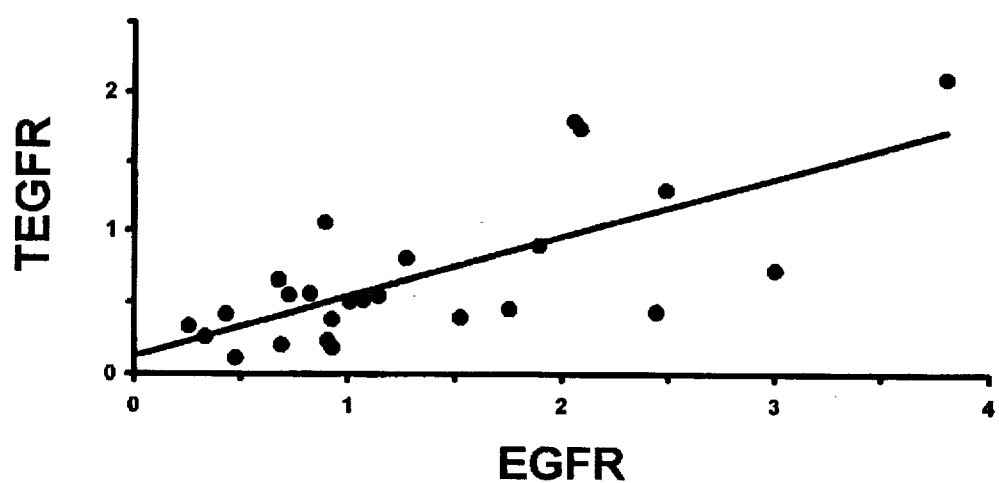

Comparable results as those obtained in the analysis of breast cancer were obtained for ovarian cancer. FIG. 5A displays the individual levels of EGFR and TEGFR obtained in these specimens. The results of this analysis indicated that EGFR and TEGFR were both expressed in all ovarian cancer specimens. FIG. 5B shows the correlation between EGFK and TEGFR levels obtained from 26 ovarian cancers. The level of TEGFR significantly correlated ($r=0.71$, $p<0.001$) to the level of EGFR. These results show that the measurement of TEGFR can detect EGFR expressing cancers and that the level of TEGFR generally correlates to the level of EGFR.

I claim:

1. An isolated nucleic acid selected from the group consisting of: nucleotides 1 through 105 and nucleotides 1713 through 1828 of SEQ ID NO:1.

2. An isolated nucleic acid selected from the group consisting of the complement of: nucleotides 1 through 105 of SEQ ID NO:1 or fragments of at least 16 nucleotides in length thereof and nucleotides 1713 through 1828 of SEQ ID NO:1 or fragments of at least 16 nucleotides in length thereof.

3. A method of detecting the nucleic acid of SEQ ID NO:1, comprising hybridizing the isolated nucleic acid of claim 2 to the nucleic acid having the sequence of SEQ ID NO:1.

4. An isolated polypeptide encoded by SEQ ID NO:1.

5. A composition comprising the isolated polypeptide of claim 4 and a pharmaceutically acceptable carrier.

6. A method for the production of polyclonal or monoclonal antibodies directed against the unique carboxy terminus, SEQ ID NO:2, of the polypeptide encoded by the isolated DNA of SEQ ID NO:1 using as an antigen a peptide consisting of at least 6 amino acids and comprising the amino acid sequence of SEQ ID NO:2 used alone or conjugated to a suitable carrier as a means for eliciting an immune response, comprising the following steps:
  a) immunizing a host animal with said antigen in suitable vehicle,
  b) harvesting antibodies from said host's blood or harvesting antibodies produced by said host's antibody-producing cells or said host's antibody-producing cells fused with another cell as a means of producing antibodies outside the original said host, said antibodies directed against the unique carboxy terminus of the polypeptide encoded by the isolated DNA of SEQ ID NO:1.

7. A purified antibody produced by the method of claim 6.

8. A method of detecting a polypeptide encoded by the isolated DNA of SEQ ID NO:1 in a human biological specimen, comprising the following steps:
  a) contacting said specimen with the antibody produced by the method of claim 6,
  b) allowing said antibody a suitable time to bind,
  c) measuring the formation of immunoreactive complexes comprising said polypeptide and said antibody.

9. The method of claim 8 wherein said human biological specimen is selected from the group consisting of fluids, tissues and their derivatives.

10. The method according to claim 8 in which the method is used in detecting the polypeptide encoded by the isolated DNA of SEQ ID NO:1 for diagnostic purposes in human cancers.

11. A method of detecting a polypeptide encoded by the isolated DNA of SEQ ID NO:1, referred to as target polypeptide, in a human biological specimen, comprising the following steps:

a) optionally separating the said target polypeptide in said specimen from interfering related polypeptides by a means based on size, charge or weight, b) contacting said specimen or said optionally separated target polypeptide with the antibody produced by the method of claim 6, c) allowing said antibody a suitable time to bind, d) measuring the formation of immunoreactive complexes.

12. The method of claim 11 wherein said human biological specimen is selected from the group consisting of fluids, tissues and their derivatives.

13. The method according to claim 11 in which the method is used in detecting the polypeptide encoded by the isolated DNA of SEQ ID NO:1 for diagnostic purposes in human cancers.

14. A method for detecting the nucleic acid of SEQ ID NO:1, referred to as target nucleic acid, in a human biological specimen using a nucleic acid isolate selected from the group consisting of nucleotides 1 through 105 of SEQ ID NO:1 or fragments of 16 nucleotides in length thereof and nucleotides 1713 through 1828 of SEQ ID NO:1 or fragments of 16 nucleotides in length thereof, comprising the following steps:

a) optionally separating the said target nucleic acid in said specimen from interfering related nucleic acids by a means based on size, charge or weight, b) adding said nucleic acid isolate to said biological specimen containing the nucleic acid encoded by SEQ ID NO:1 in the form of RNA or DNA, c) allowing said nucleic acid isolate to hybridize or anneal to said target nucleic acid, d) measuring the amount of hybridized or annealed nucleic acid complex or measuring the amount of a nucleic acid product formed that is derived from the target nucleic acid, initially present in said specimen, following amplifying said nucleic acid product.

15. The method of claim 14 wherein said human biological specimen is selected from the group consisting of fluids, tissues and their derivatives.

16. The method according to claim 14 in which the method is used in detecting the nucleic acid of SEQ ID NO:1 for diagnostic purposes in human cancers.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1868 bases
        ( B ) TYPE: nucleic acid
        ( C ) STRANDEDNESS: Single
        ( D ) TOPOLOGY: linear ( i i ) MOLECULE TYPE: cDNA ( v i ) ORIGINAL SOURCE:
        ( A ) ORGANISM: Homo sapiens
        ( F ) TISSUE TYPE: Term Placenta ( v i i ) IMMEDIATE SOURCE:
        ( A ) LIBRARY: cDNA ( i x ) FEATURE:
        ( D ) OTHER INFORMATION: Deduced amino acid length of 381. Putative signal peptide Met-1 to Ala-24.

( x i ) SEQUENCE DESCRIPTION: SEQ ID NO:1:

```
GAAAACAGGC  TGGGCCCGGT  GGCTCACTCC  TGTAATCCCA  GCACTTTGGG   50

AGGTTGAGGT  GGGCGGATCA  CCTGAGGTCA  GGAGTTTGAG  ACCAGCCGGC  100

GGGAGTGGCC  TTGGGTCCCC  GCTGCTGGTT  CTCCTCCCTC  CTCCTCGCAT  150

TCTCCTCCTC  CTCTGCTCCT  CCCGATCCCT  CCTCCGCCGC  CTGGTCCCTC  200

CTCCTCCCGC  CCTGCCTCCC  CGCGCCTCGG  CCCGCGCGAG  CTAGACGTCC  250

GGGCAGCCCC  CGGCGCACCG  CGGCCGCAGC  AGCCTCCTCC  CCCCGCACGG  300

TGTGAGCGCC  CGCCGCGGCC  GAGGCGGCCG  GAGTCCCGAG  CTAGCCCCGG  350

CGGCCGCCGC  CGCCCAGACC  GGACGACAGG  CCACCTCGTC  GGCGTCCGCC  400

CGAGTCCCCG  CCTCGCCGCC  AACGCCACAA  CCACCGCGCA  CGGCCCCCTG  450

ACTCCGTCCA  GTATTGATCG  GGAGAGCCGG  AGCGAGCTCT  TCGGGGAGCA  500

GCG  ATG  CGA  CCC  TCC  GGG  ACG  GCC  GGG  GCA  GCG  CTC  CTG  GCG  CTG   545
                     Met  Arg  Pro  Ser  Gly  Thr  Ala  Gly  Ala  Ala  Leu  Leu  Ala  Leu
                      -1       -5                           -10
```

```
CTG  GCT  GCG  CTC  TGC  CCG  GCG  AGT  CGG  GCT  CTG  GAG  GAA  AAG  AAA  590
Leu  Ala  Ala  Leu  Cys  Pro  Ala  Ser  Arg  Ala  Leu  Glu  Glu  Lys  Lys
-15            -20                           1                        5

GTT  TGC  CAA  GGC  ACG  AGT  AAC  AAG  CTC  ACG  CAG  TTG  GGC  ACT  TTT  635
Val  Cys  Gln  Gly  Thr  Ser  Asn  Lys  Leu  Thr  Gln  Leu  Gly  Thr  Phe
10             15                      20

GAA  GAT  CAT  TTT  CTC  AGC  CTC  CAG  AGG  ATG  TTC  AAT  AAC  TGT  GAG  680
Glu  Asp  His  Phe  Leu  Ser  Leu  Gln  Arg  Met  Phe  Asn  Asn  Cys  Glu
25             30                      35

GTG  GTC  CTT  GGG  AAT  TTG  GAA  ATT  ACC  TAT  GTG  CAG  AGG  AAT  TAT  725
Val  Val  Leu  Gly  Asn  Leu  Glu  Ile  Thr  Tyr  Val  Gln  Arg  Asn  Tyr
40             45                      50

GAT  CTT  TCC  TTC  TTA  AAG  ACC  ATC  CAG  GAG  GTG  GCT  GGT  TAT  GTC  770
Asp  Leu  Ser  Phe  Leu  Lys  Thr  Ile  Gln  Glu  Val  Ala  Gly  Tyr  Val
55             60                      65

CTC  ATT  GCC  CTC  AAC  ACA  GTG  GAG  CGA  ATT  CCT  TTG  GAA  AAC  CTG  815
Leu  Ile  Ala  Leu  Asn  Thr  Val  Glu  Arg  Ile  Pro  Leu  Glu  Asn  Leu
70             75                      80

CAG  ATC  ATC  AGA  GGA  AAT  ATG  TAC  TAC  GAA  AAT  TCC  TAT  GCC  TTA  860
Gln  Ile  Ile  Arg  Gly  Asn  Met  Tyr  Tyr  Glu  Asn  Ser  Tyr  Ala  Leu
85             90                      95

GCA  GTC  TTA  TCT  AAC  TAT  GAT  GCA  AAT  AAA  ACC  GGA  CTG  AAG  GAG  905
Ala  Val  Leu  Ser  Asn  Tyr  Asp  Ala  Asn  Lys  Thr  Gly  Leu  Lys  Glu
100            105                     110

CTG  CCC  ATG  AGA  AAT  TTA  CAG  GAA  ATC  CTG  CAT  GGC  GCC  GTG  CGG  950
Leu  Pro  Met  Arg  Asn  Leu  Gln  Glu  Ile  Leu  His  Gly  Ala  Val  Arg
115            120                     125

TTC  AGC  AAC  AAC  CCT  GCC  CTG  TGC  AAC  GTG  GAG  AGC  ATC  CAG  TGG  995
Phe  Ser  Asn  Asn  Pro  Ala  Leu  Cys  Asn  Val  Glu  Ser  Ile  Gln  Trp
130            135                     140

CGG  GAC  ATA  GTC  AGC  AGT  GAC  TTT  CTC  AGC  AAC  ATG  TCG  ATG  GAC  1040
Arg  Asp  Ile  Val  Ser  Ser  Asp  Phe  Leu  Ser  Asn  Met  Ser  Met  Asp
145            150                     155

TTC  CAG  AAC  CAC  CTG  GGC  AGC  TGC  CAA  AAG  TGT  GAT  CCA  AGC  TGT  1085
Phe  Gln  Asn  His  Leu  Gly  Ser  Cys  Gln  Lys  Cys  Asp  Pro  Ser  Cys
160            165                     170

CCC  AAT  GGG  AGC  TGC  TGG  GGT  GCA  GGA  GAG  GAG  AAC  TGC  CAG  AAA  1130
Pro  Asn  Gly  Ser  Cys  Trp  Gly  Ala  Gly  Glu  Glu  Asn  Cys  Gln  Lys
175            180                     185

CTG  ACC  AAA  ATC  ATC  TGT  GCC  CAG  CAG  TGC  TCC  GGG  CGC  TGC  CGT  1175P
Leu  Thr  Lys  Ile  Ile  Cys  Ala  Gln  Gln  Cys  Ser  Gly  Arg  Cys  Arg
190            195                     200

GGC  AAG  TCC  CCC  AGT  GAC  TGC  TGC  CAC  AAC  CAG  TGT  GCT  GCA  GGC  1220
Gly  Lys  Ser  Pro  Ser  Asp  Cys  Cys  His  Asn  Gln  Cys  Ala  Ala  Gly
205            210                     215

TGC  ACA  GGC  CCC  CGG  GAG  AGC  GAC  TGC  CTG  GTC  TGC  CGC  AAA  TTC  1265
Cys  Thr  Gly  Pro  Arg  Glu  Ser  Asp  Cys  Leu  Val  Cys  Arg  Lys  Phe
220            225                     230

CGA  GAC  GAA  GCC  ACG  TGC  AAG  GAC  ACC  TGC  CCC  CCA  CTC  ATG  CTC  1310
Arg  Asp  Glu  Ala  Thr  Cys  Lys  Asp  Thr  Cys  Pro  Pro  Leu  Met  Leu
235            240                     245

TAC  AAC  CCC  ACC  ACG  TAC  CAG  ATG  GAT  GTG  AAC  CCC  GAG  GGC  AAA  1355
Tyr  Asn  Pro  Thr  Thr  Tyr  Gln  Met  Asp  Val  Asn  Pro  Glu  Gly  Lys
250            255                     260

TAC  AGC  TTT  GGT  GCC  ACC  TGC  GTG  AAG  AAG  TGT  CCC  CGT  AAT  TAT  1400
Tyr  Ser  Phe  Gly  Ala  Thr  Cys  Val  Lys  Lys  Cys  Pro  Arg  Asn  Tyr
265            270                     275

GTG  GTG  ACA  GAT  CAC  GGC  TCG  TGC  GTC  CGA  GCC  TGT  GGG  GCC  GAC  1445
Val  Val  Thr  Asp  His  Gly  Ser  Cys  Val  Arg  Ala  Cys  Gly  Ala  Asp
280            285                     290
```

-continued

```
AGC TAT GAG ATG GAG GAA GAC GGC GTC CGC AAG TGT AAG AAG TGC  1490
Ser Tyr Glu Met Glu Glu Asp Gly Val Arg Lys Cys Lys Lys Cys
295                     300                 305

GAA GGG CCT TGC CGC AAA GTG TGT AAC GGA ATA GGT ATT GGT GAA  1535
Glu Gly Pro Cys Arg Lys Val Cys Asn Gly Ile Gly Ile Gly Glu
310                 315                 320

TTT AAA GAC TCA CTC TCC ATA AAT GCT ACG AAT ATT AAA CAC TTC  1580
Phe Lys Asp Ser Leu Ser Ile Asn Ala Thr Asn Ile Lys His Phe
325             330                 335

AAA AAC TGC ACC TCC ATC AGT GGC GAT CTC CAC ATC CTG CCG GTG  1625
Lys Asn Cys Thr Ser Ile Ser Gly Asp Leu His Ile Leu Pro Val
340             345                 350

GCA TTT AGG GGT GAC TCC TTC ACA CAT ACT CCC CCT CTG GAT CCA  1670
Ala Phe Arg Gly Asp Ser Phe Thr His Thr Pro Pro Leu Asp Pro
355             360                 365

CAG GAA CTG GAT ATT CTG AAA ACC GTA AAG GAA ATC ACA GGT TTG  1715
Gln Glu Leu Asp Ile Leu Lys Thr Val Lys Glu Ile Thr Gly Leu
370             375                 380

AGC TGAATTATCA CATGAATATA AATGGGAAAT CAGTGTTTTA GAGAGAGAAC   1768
Ser

TTTTCGACAT ATTTCCTGTT CCCTTGGAAT AAAAACATTT CTTCTGAAAT       1818

TTTACCGTTA AAAAAAAAAA AAAAAAAAAA AAAAAAAAAA AAAAAAAAA        1868
```

( 2 ) INFORMATION FOR SEQ ID NO:2:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: protein ( v ) FRAGMENT TYPE: C-terminal ( i x ) FEATURE:
  ( D ) OTHER INFORMATION: C-terminal of protein
        encoded by nucleic acid of SEQ ID NO:1.

( x i ) SEQUENCE DESCRIPTION: SEQ ID NO:2:

```
Glu Ile Thr Gly Leu Ser   6
 1             5
```